US005964898A

United States Patent [19]
Cotteret et al.

[11] Patent Number: 5,964,898
[45] Date of Patent: Oct. 12, 1999

[54] COMPOSITION FOR THE OXIDATION DYEING OF KERATINOUS FIBERS COMPRISING 2-(β-HYDROXYETHYL)-PARA-PHENYLENEDIAMINE, 2-METHYLRESORCINOL AND RESORCINOL, AND DYEING PROCESS USING SUCH A COMPOSITION

[75] Inventors: Jean Cotteret, Verneuil sur Seine; Marie-Pascale Audousset, Asnieres, both of France

[73] Assignee: L'Oreal, Paris, France

[21] Appl. No.: 08/984,140

[22] Filed: Dec. 3, 1997

Related U.S. Application Data

[63] Continuation of application No. 08/460,870, Jun. 5, 1995, abandoned.

[30] Foreign Application Priority Data

Jun. 21, 1994 [FR] France .................................. 94 07582

[51] Int. Cl.⁶ ..................................... A61K 7/13
[52] U.S. Cl. ........................... 8/410; 8/408; 8/416; 8/424
[58] Field of Search ................ 8/406, 408, 410, 8/424, 416

[56] References Cited

U.S. PATENT DOCUMENTS

| 4,863,480 | 9/1989 | Bugaut et al. .............................. 8/408 |
| 4,954,131 | 9/1990 | Bugaut et al. .............................. 8/421 |
| 4,985,042 | 1/1991 | Bugaut et al. .............................. 8/421 |
| 5,053,051 | 10/1991 | Tennigkeit et al. ......................... 8/406 |
| 5,089,257 | 2/1992 | Schrader et al. .......................... 424/70 |
| 5,137,538 | 8/1992 | Madrange et al. ......................... 8/410 |
| 5,224,965 | 7/1993 | Clausen et al. ............................ 8/411 |
| 5,344,464 | 9/1994 | Madrange et al. ......................... 8/410 |
| 5,494,489 | 2/1996 | Akram et al. .............................. 8/408 |
| 5,542,953 | 8/1996 | Balzer et al. .............................. 8/416 |

FOREIGN PATENT DOCUMENTS

| 0 400 330 | 12/1990 | European Pat. Off. . |
| 30 31 535 | 4/1982 | Germany . |
| 2 239 265 | 6/1991 | United Kingdom . |

*Primary Examiner*—Mark Kopec
*Assistant Examiner*—Caroline D. Liott
*Attorney, Agent, or Firm*—Finnegan, Henderson, Farabow, Garrett & Dunner, L.L.P.

[57] ABSTRACT

An oxidation dyeing composition for keratinous fibers containing, in a medium appropriate for dyeing, at least one oxidation dye precursor selected from 2-(β-hydroxyethyl)-para-phenylenediamine or its acid addition salts, at least one first coupler selected from 2-methylresorcinol or at least one acid addition salt thereof, and at least one second coupler selected from resorcinol or at least one acid addition salt thereof, and methods for dyeing keratinous fibers, especially hair, with such compositions.

12 Claims, No Drawings

COMPOSITION FOR THE OXIDATION DYEING OF KERATINOUS FIBERS COMPRISING 2-(β-HYDROXYETHYL)-PARA-PHENYLENEDIAMINE, 2-METHYLRESORCINOL AND RESORCINOL, AND DYEING PROCESS USING SUCH A COMPOSITION

This is a continuation of application Ser. No. 08/460,870, filed Jun. 5, 1995, now abandoned which is incorporated herein by reference.

The present invention relates to a composition for the oxidation dyeing of keratinous fibers and in particular of human keratinous fibers comprising, in combination, 2-(β-hydroxyethyl)-para-phenylenediamine, 2-methylresorcinol and resorcinol. It also relates to the use of such a composition.

It is known to dye keratinous fibers, and in particular human hair, with dyeing compositions containing oxidation dye precursors, in particular ortho- or para-phenylenediamines or ortho- or para-aminophenols, generally known as "oxidation bases", in combination with couplers, also known as coloring modifiers, more particularly meta-phenylenediamines, meta-aminophenols and meta-diphenols, which make it possible to modify and enrich with highlights the "foundation" colorings obtained with the condensation products of oxidation bases.

The search, in the field of oxidation hair dyeing, is for oxidation dye precursors and couplers capable of producing, when they are combined, shades having a satisfactory resistance to light, to washes, to bad weather, to perspiration and to the various hair treatments to which hair may be subjected.

Until now, these shades have been obtained with dyes based on para-phenylenediamine. However, the use of para-phenylenediamine appears for some time to have been questioned, especially for toxicological reasons.

Also, in replacing para-phenylenediamine, it has already been proposed, in Patent Application Wo 80/00214, to use para-phenylenediamine derivatives monohydroxyalkylated in the 2-position on the benzene ring.

Unfortunately, it turns out that the shades which are obtained with dyes using para-phenylenediamine derivatives monohydroxyalkylated in the 2-position on the benzene ring do not have a satisfactory resistance to shampoos, to light and to perspiration, especially when the hair to be dyed is hair which has been sensitized by hair treatments of chemical type, in particular permanent deformation or bleaching treatments.

In Patent EP-0,400,330 B1, moreover, a description has very particularly been given of a combination between 2-(β-hydroxyethyl)-para-phenylenediamine and a coupler chosen from resorcinol, 4-chlororesorcinol, 2-methylresorcinol, 3,4-methylenedioxyphenol, 3-aminophenol and N-(2-hydroxyethyl)-3,4-methylenedioxyaniline. However, it is there again observed that the combinations of 2-(β-hydroxyethyl)-para-phenylenediamine with one or other of the couplers mentioned above produce dyes which have little resistance to shampoos, to light and to perspiration, in particular in the case of hair sensitized by permanent deformation treatments or bleaching treatments, which greatly limits the practical advantage of such combinations in the field of hair dyeing.

Now, after much research directed at this question, the 3-inventors have discovered that it is possible to obtain new non-toxic dyes which produce shades which are particularly highly resistant, at once to shampoos, to light and to perspiration, by combining 2-(β-hydroxyethyl)-para-phenylenediamine with, jointly, 2-methylresorcinol and resorcinol.

This discovery is the basis of the present invention.

The subject of the present invention is thus an oxidation dyeing composition for keratinous fibers, in particular for human keratinous fibers, such as hair, comprising, in a medium appropriate for dyeing, at least one oxidation dye precursor selected from 2-(β-hydroxyethyl)-para-phenylenediamine and its acid addition salts and at least one coupler selected from a combination of 2-methylresorcinol or at least one acid addition salt thereof with resorcinol or at least one acid addition salt thereof.

In particular, and as will be shown in the examples given below, the new dyes thus obtained make it possible to produce, on hair which has nevertheless been sensitized by permanent deformation or bleaching treatments, shades which are much more resistant, at once to shampoos, to light and to perspiration, than those containing i) 2-(β-hydroxyethyl)-para-phenylenediamine in combination with 2-methylresorcinol or ii) 2-(β-hydroxyethyl)-para-phenylenediamine in combination with resorcinol.

Another subject of the invention relates to the ready-to-use composition containing the various agents used for dyeing keratinous fibers defined above and an oxidizing agent.

The invention is also targeted at a process for dyeing keratinous fibers, and in particular human keratinous fibers such as hair, which comprises applying to these fibers at least one composition (A) containing, in a medium appropriate for dyeing, at least one oxidation dye precursor and at least two couplers as they have been defined above, the color being developed at alkaline, neutral or acidic pH using an oxidizing agent which is added to the composition (A) only at the time of use or which is present in a composition (B) separately applied simultaneously or sequentially.

Another subject of the invention is multi-compartment dyeing devices or "kits", the first compartment of which contains at least 2-(β-hydroxyethyl)-para-phenylenediamine, as oxidation dye precursor, and at least the combination of 2-methylresorcinol and resorcinol, as couplers, and the second compartment of which contains an oxidizing agent.

Other characteristics, aspects, subjects and advantages of the invention will become still more clearly apparent on reading the description and examples which follow.

The acid salts which can be used according to the invention are preferably chosen from hydrochlorides, sulphates, hydrobromides and tartrates.

The concentration of oxidation dye precursor, or of its salts, can preferably vary from 0.01 to 10% by weight, approximately, with respect to the total weight of the dyeing composition and more preferably from 0.05 to 5% by weight, approximately.

The concentration of 2-methylresorcinol or of its salts can preferably vary from 0.005 to 5% by weight, approximately, with respect to the total weight of the dyeing composition and more preferably from 0.05 to 3% by weight, approximately.

The concentration of resorcinol or of its salts can preferably vary from 0.005 to 5% by weight, approximately, with respect to the total weight of the dyeing composition and more preferably from 0.05 to 3% by weight, approximately.

The oxidizing agent is preferably chosen from hydrogen peroxide, urea hydrogen peroxide, alkali metal bromates and persalts such as perborates and persulphates. The use of hydrogen peroxide is particularly preferred.

The composition (A), which contains the combination of the dyes such as described above, can generally have a pH of from 3 to 11 which can be adjusted to the chosen value either by means of basifying agents commonly used in dyeing keratinous fibers, such as aqueous ammonia, alkali metal carbonates, alkanolamines, for example mono-, di- and triethanolamines and their derivatives, sodium hydroxide or potassium hydroxide or the compounds of formula:

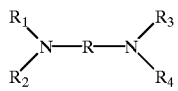

in which R is a propylene residue optionally substituted by a hydroxyl group or a $C_1$–$C_4$ alkyl radical and $R_1$, $R_2$, $R_3$ and $R_4$, simultaneously or independently of one another, represent a hydrogen atom or a $C_1$–$C_4$ alkyl or $C_1$–$C_4$ hydroxyalkyl radical, or by means of conventional acidifying agents, such as inorganic or organic acids such as, for example, hydrochloric, tartaric, citric and phosphoric acids.

The pH of the composition (B) containing the oxidizing agent such as defined above is such that, after mixing with the composition (A), the pH of the composition applied to human keratinous fibers preferably varies from 3 to 11. It is adjusted to the desired value using acidifying agents or optionally basifying agents which are well known in the state of the art, such as those described above.

As indicated above, the oxidizing composition (B) preferably consists of a hydrogen peroxide solution.

According to a preferred embodiment of the dyeing process of the invention, the dyeing composition (A) described above is mixed, at the time of use, with an oxidizing solution in an amount sufficient to develop a coloring. The mixture obtained is then applied to human keratinous fibers and left exposed for 5 to 40 minutes, preferably 15 to 30 minutes, after which the fibers are rinsed, washed with a shampoo, rinsed again and dried.

The dyeing compositions can also contain, in addition to the dyes defined above, other couplers and/or direct dyes, especially for modifying the shades or for enriching them with highlights.

The dyeing compositions can also contain anti-oxidizing agents. The latter can be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid and are then generally present in an amount from approximately 0.05 to 1.5% by weight with respect to the total weight of the composition.

The dyeing compositions also contain, in their preferred embodiment, surface-active agents which are well known in the art in a general amount of from approximately 0.5 to 55% by weight, and preferably from 2 to 50% by weight, with respect to the total weight of the composition, organic solvents, in an amount of from approximately 1 to 40% by weight, and in particular from 5 to 30% by weight, with respect to the total weight of the composition, or any other adjuvant which is cosmetically acceptable and known in the prior art in oxidation hair dyeing.

The composition applied to the hair can be provided in various forms, such as in liquid, cream or gel form or in any other form appropriate for carrying out dyeing of keratinous fibers, and especially of human hair. In particular, it can be packaged under pressure in an aerosol canister in the presence of a propellant and can form a foam.

Concrete examples illustrating the invention will now be given. The first step will be to define the tests used to evaluate the performances of the oxidation dyes according to the invention as regards their resistance to shampoos, to light and to perspiration.

Resistance to Shampoos (Ahiba-Texomat Machine):

Locks of dyed hair were placed in a basket which was immersed in a solution of a standard shampoo. The basket was subjected to a vertical to-and-fro movement of variable frequency and to a rotational movement which reproduced the action of manual rubbing, which led to the formation of foam.

After testing for 3 minutes, the locks were removed and were rinsed and then dried. The dyed locks could be subjected to a number of consecutive shampoo tests.

Resistance to Light (Xenotest):

Dyed hair was fixed to a support (cardboard or plastic). These supports were arranged on sample holders which rotated around a Xenon lamp for a period of time varying from 20 to 80 hours at a degree of humidity varying from 25 to 75% RH (Relative Humidity) and at a temperature of 25° C.

Resistance to Perspiration:

A synthetic sweat solution with the following composition was used:

| | |
|---|---|
| NaCl | 1 g |
| Potassium hydrogenphosphate | 0.1 g |
| Histidine | 0.025 g |
| Lactic acid q.s. | pH 3.2 |
| Digtilled water | q.s. for 100 g |

The locks of dyed hair were immersed in a crystallizing dish covered with a watch glass and containing this sweat solution and were left to stand for from 20 to 50 hours at 37° C. The locks were then rinsed and dried.

EXAMPLE 1

The following dyeing composition, in accordance with the invention, was prepared:

| | |
|---|---|
| 2-(β-Hydroxyethyl)-para-phenylene-diamine dihydrochloride | 0.60 g |
| 2-Methylresorcinol | 0.20 g |
| Resorcinol | 0.20 g |
| Oleyl alcohol polyglycerolated with 4 mol of glycerol, containing 78% of active materials (A.M.) | 5.7 g A.M. |
| Oleyl alcohol polyglycerolated with 2 mol of glycerol | 4.0 g |
| Oleic acid | 3.0 g |
| Oleylamine containing 2 mol of ethylene oxide, soid under the name Ethomeen 012 by the Company Akzo | 7.0 g |
| Diethylaminopropyl laurylamino-succinamate, sodium salt, containing 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulphite as an aqueous solution containing 35% of A.M. | 0.46 g A.M. |
| Ammonium acetate | 0.8 g |
| Anti-oxidizing agent, sequestering agent | q.s. |
| Fragrance, preserving agent | q.s. |
| Aqueous ammonia solution containing 20% of $NH_3$ | 2.0 g A.M. |
| Demineralized water | q.s. for 100.0 g |

Two comparative compositions were prepared in parallel which contained, as replacement for the ternary coloring combination according to the invention comprising 2-(β-hydroxyethyl)-para-phenylenediamine dihydrochloride+2-methylresorcinol+resorcinol, the following binary coloring combinations:

Comparative Composition (A):
2-(β-Hydroxyethyl)-para-phenylenediamine dihydrochloride (0.6 g)+2-methylresorcinol (0.4 g), Comparative composition (B):
2-(β-Hydroxyethyl)-para-phenylenediamine dihydrochloride (0.6 g)+resorcinol (0.4 g).

At the time of use, each of these three compositions was mixed, weight for weight, with hydrogen peroxide assaying at 20 volumes (6% by weight), with a pH of 3.

Three mixtures were obtained with pH values of 9.8.

These mixtures were then applied to the hair to be dyed for 30 minutes; the hair was then rinsed, washed with a shampoo, rinsed again and finally dried.

Evaluation of the Resistance to Shampoos: After having dyed hair of the same nature (permed grey hair containing 90% of white hairs) with each of the three above compositions respectively: the composition of the invention and the two comparative compositions (A) and (B), the dyed hair was,subjected to the test of resistance to shampoos (3 shampoos) described above.

The deterioration in the color between the dyed hair and that dyed which has been subjected to three shampoo tests was expressed by means of the Nickerson equation which defines the color variation indices:

$$\Delta E = 0.4 C_0 \Delta H + 6 \Delta V + 3 \Delta C;$$

this equation is described in the publication "Journal of the Optical Society of America", 1944, Sept., Vol. 34, No. 9, p. 550–570, the parameters H, V and C representing the parameters of the Munsell notation (ASTM Standard D 1535–68), which defines the color (H denoting the shade or Hue, V denoting the intensity or Value, C denoting the purity or Chromaticity and $C_0$ denoting the purity of the lock with respect to which it is desired to evaluate the difference in color).

The deteriorations in the color recorded with the composition according to the invention and those of the comparative compositions (A) and (B) are combined in Table I below:

TABLE I

| Dyeing composition | Variation in color between dyed hair and dyed hair which has been subjected to three shampoo tests (ΔE) |
|---|---|
| Composition of the invention | 1.48 |
| Comparative composition (A) | 4.15 |
| Comparative composition (B) | 3.25 |

As the deterioration in color (ΔE) became greater as the figure indicated became higher, the dyeing composition according to the invention was thus clearly observed, unexpectedly and surprisingly, to have a much better resistance to shampoos.

Evaluation of the Resistance to Light:

After having dyed hair of the same nature (bleached brown hair) with each of the three above compositions respectively: the composition of the invention and the two comparative compositions (A) and (B), the dyed hair was subjected to the test of resistance to light described above.

The deterioration in the color between the dyed hair and that dyed which has been subjected to a light test for 40 hours was expressed by means of the Nickerson equation described above.

The deteriorations in the color recorded with the composition according to the invention and those of the comparative compositions (A) and (B) are combined in Table II below:

TABLE II

| Dyeing composition | Variation in color between dyed hair and dyed hair which has been subjected to a light test for 40 h (ΔE) |
|---|---|
| Composition of the invention | 1.48 |
| Comparative composition (A) | 2.86 |
| Comparative composition (B) | 2.74 |

As the deterioration in color (ΔE) became greater as the figure indicated became higher, the dyeing composition according to the invention was thus clearly observed, unexpectedly and surprisingly, to have a markedly better resistance to light.

Evaluation of the Resistance to Perspiration:

After having dyed hair of the same nature (bleached brown hair) with each of the three above compositions respectively: the composition of the invention and the two comparative compositions (A) and (B), the dyed hair was subjected to the test of resistance to perspiration described above (contact time: 48 hours).

The deterioration in the color between the dyed hair and that dyed which has been subjected to a perspiration test was expressed by means of the Nickerson equation described above.

The deteriorations in the color recorded with the composition according to the invention and those of the comparative compositions (A) and (B) are combined in Table III below:

TABLE III

| Dyeing composition | Variation in color between dyed hair and dyed hair which has been subjected to a perspiration test (ΔE) |
|---|---|
| Composition of the invention | 1.74 |
| Comparative composition (A) | 3.30 |
| Comparative composition (B) | 4.96 |

As the deterioration in color (ΔE) became greater as the figure indicated became higher, the dyeing composition according to the invention was thus clearly observed, unexpectedly and surprisingly, to have a much better resistance to perspiration.

What is claimed is:

1. An oxidation dyeing composition (A) comprising, in a medium appropriate for dyeing, at least one oxidation dye precursor selected from 2-(β-hydroxyethyl)-para-phenylenediamine or acid addition salts thereof, said oxidation dye precursor being present in a concentration of from 0.01 to 10% by weight relative to the total weight of the composition, at least one first coupler selected from 2-methylresorcinol or acid additional salts thereof, said first coupler being present in a concentration of from 0.01 to 5% by weight relative to the total weight of the composition, and at least one second coupler selected from resorcinol or acid addition salts thereof, said second coupler being present in a concentration of from 0.01 to 5% by weight relative to the total weight of the composition.

2. The dyeing composition according to claim 1, wherein said acid addition salts are selected from hydrochlorides, sulphates, hydrobromides or tartrates.

3. The dyeing composition according to claim 1, wherein said at least one oxidation dye precursor is present in a concentration of from 0.05 to 5% by weight; said 2-methylresorcinol or said at least one acid addition salt thereof is present in a concentration of from 0.05 to 3% by weight; and said resorcinol or said at least one acid addition salt thereof is present in a concentration of from 0.05 to 3% by weight with respect to the total weight of the composition.

4. The dyeing composition according to claim 1, which is ready-to-use for dyeing keratinous fibers, wherein said composition further contains an oxidizing agent and has a pH from 3 to 11.

5. A process for dyeing keratinous fibers comprising the steps of:

applying to said fibers a dyeing composition (A) according to claim 1 and developing a color in alkaline, neutral or acidic medium with an oxidizing agent which is added to said composition (A) before application of said dyeing composition (A) to said fibers or which is present in a composition (B) separately applied to said fibers simultaneously along with said dyeing composition (A) or sequentially with respect to said dyeing composition (A).

6. The process of claim 5, wherein said keratinous fibers are human keratinous fibers.

7. The process of claim 6, wherein said human keratinous fibers are hair.

8. A multi-compartment device or kit for dyeing keratinous fibers, wherein said device contains at least two compartments, one of which contains an oxidation dyeing composition (A) as defined in claim 1 and another of which contains a composition (B) comprising an oxidizing agent in a medium appropriate for dyeing.

9. The device of claim 8, wherein said keratinous fibers are human keratinous fibers.

10. The device of claim 9, wherein said human keratinous fibers are hair.

11. A method for dyeing human keratinous fibers comprising the step of applying a composition (A) and said composition (B) to said human keratinous fibers, said composition (A) and said composition (B) being obtained from a multi-compartment device or kit for dyeing keratinous fibers wherein said device contains at least two compartments, one of which contains an oxidation dyeing composition (A) as defined in claim 1 and another of which contains a composition (B) comprising an oxidizing agent in a medium appropriate for dyeing.

12. The method of claim 11, wherein said human keratinous fibers are hair.

* * * * *